(12) United States Patent
Schwarz et al.

(10) Patent No.: US 6,656,916 B1
(45) Date of Patent: Dec. 2, 2003

(54) GLUCOCORTICOID ENHANCEMENT OF GENE EXPRESSION

(75) Inventors: Lindsay Schwarz, Conroe, TX (US); Vernon Knight, Houston, TX (US); Jennifer Lee Johnson, The Woodlands, TX (US)

(73) Assignee: Research Development Foundation, Carson City, NV (US)

( * ) Notice: Subject to any disclaimer, the term of this patent is extended or adjusted under 35 U.S.C. 154(b) by 1058 days.

(21) Appl. No.: 08/709,554

(22) Filed: Sep. 6, 1996

Related U.S. Application Data

(60) Provisional application No. 60/003,418, filed on Sep. 8, 1995.

(51) Int. Cl.[7] .............................................. A61K 48/00
(52) U.S. Cl. ...................... 514/44; 435/320.1; 435/455; 435/458; 424/93.2
(58) Field of Search .............................. 514/44; 424/520, 424/93.2; 435/455, 325, 320.1, 458, 69.1, 91.32; 935/33, 34, 43, 52, 55, 60, 70

(56) References Cited

U.S. PATENT DOCUMENTS

| 5,512,483 A | * | 4/1996 | Mader | 435/320.1 |
| 5,756,353 A | * | 5/1998 | Debs | 435/375 |
| 5,830,430 A | * | 11/1998 | Unger | 424/1.21 |

OTHER PUBLICATIONS

Borson et al., American J. of Physiology, 260, 2 Pt 1, L83–9, 1991.*

Ming et al. B–Adrenergic receptors and angiotensinogen gene expression in mouse gepatoma cells in vitro pp. 105–109, 1995.*

Malone et al. Dexamethasome enhancement of gene expression after direct hepatic DNA injection vol 269,No. 47 pp. 29903–29907, 1994.*

Hill et al. Methods in Cell Biol. 43 PT A:247–62, 1994, Jan. 27, 1996.

Ido et al. Cancer Res. Jul. 1995, 55:3105–3109, Jan. 27, 1996.

Morsy et al JAMA, Nov. 1993, vol. 270, 19:2338–2345, Jan. 27, 1997.

Gunzburg et al. Mol. Med. Today 1995:410–417, vol. 1, Jan. 27, 1997.

Coghlan. New Scientist, Nov. 1995, p. 14, Jan. 27, 1997.

Marshall. Science Dec. 1995:1751, vol. 171, Jan. 27, 1997.

Ledley. Human Gene Therapy 1995, 6:1129–1144, Jan. 27, 1997.

* cited by examiner

*Primary Examiner*—Dave T. Nguyen
(74) *Attorney, Agent, or Firm*—Benjamin Aaron Adler

(57) ABSTRACT

The present invention provides a method of increasing the cellular expression of a gene in a biological tissue after delivery of said gene to an animal, comprising the step of: administering to said animal a pharmacologically effective dose of a glucocorticoid in an amount sufficient to increase the cellular expression of said gene. Also provided is a various method of treating a pathophysiological state in a human by increasing cellular expression of a gene after delivery of said gene into a biological tissue of an animal in need of such treatment, comprising the step of: administering to said animal a pharmacologically effective dose of a glucocorticoid in an amount sufficient to increase the cellular expression of said gene.

11 Claims, 12 Drawing Sheets

FIG 7. KINETICS

```
                           SEQUENCE LISTING (1) GENERAL INFORMATION:

(iii) NUMBER OF SEQUENCES:  3

(2) INFORMATION FOR SEQ ID NO:1:

(i) SEQUENCE CHARACTERISTICS:
          (A) LENGTH:  50
          (B) TYPE: nucleic acid
          (C) STRANDEDNESS: single
          (D) TOPOLOGY: linear (ii) MOLECULE TYPE:
          (A) DESCRIPTION: other nucleic acid (iii) HYPOTHETICAL: No (iv) ANTI-SENSE: No (vi) ORIGINAL SOURCE:
          (B) STRAIN:  N/A
          (C) INDIVIDUAL ISOLATE:  N/A
          (D) DEVELOPMENTAL STAGE: N/A
          (F) TISSUE TYPE:  N/A
          (G) CELL TYPE: N/A
          (H) CELL LINE: N/A (xi) SEQUENCE DESCRIPTION: SEQ ID NO:1:

GAACATCGAT GACAAGCTTA GGTATCGATA CACCTCGCGG AAACCGACAT                   50

(2) INFORMATION FOR SEQ ID NO:2:

(i) SEQUENCE CHARACTERISTICS:
          (A) LENGTH:  22
          (B) TYPE: nucleic acid
          (C) STRANDEDNESS: single
          (D) TOPOLOGY: linear (ii) MOLECULE TYPE:
          (A) DESCRIPTION: other nucleic acid (iii) HYPOTHETICAL: No (iv) ANTI-SENSE: No (vi) ORIGINAL SOURCE:
          (B) STRAIN: N/A
          (C) INDIVIDUAL ISOLATE: N/A
          (D) DEVELOPMENTAL STAGE: N/A
          (F) TISSUE TYPE: N/A
          (G) CELL TYPE: N/A
          (H) CELL LINE: N/A (xi) SEQUENCE DESCRIPTION: SEQ ID NO:2:

GAGAATCCGA CGGGTTGTTA CT                                                 22

(2) INFORMATION FOR SEQ ID NO:3:

(i) SEQUENCE CHARACTERISTICS:
          (A) LENGTH:  31
          (B) TYPE: nucleic acid
          (C) STRANDEDNESS: single
          (D) TOPOLOGY: linear (ii) MOLECULE TYPE:
```

-continued

```
        (A) DESCRIPTION: other nucleic acid (iii) HYPOTHETICAL: No (iv) ANTI-SENSE: No (vi) ORIGINAL SOURCE:
         (B) STRAIN:
         (C) INDIVIDUAL ISOLATE:
         (D) DEVELOPMENTAL STAGE:
         (F) TISSUE TYPE:
         (G) CELL TYPE:
         (H) CELL LINE:

(xi) SEQUENCE DESCRIPTION: SEQ ID NO:3:

GAACATCGAT GAACAAGCTT AGGTATCGAT A                                      31
```

GLUCOCORTICOID ENHANCEMENT OF GENE EXPRESSION

This application claims priority under 119(e) to Provisional Application U.S. Ser. No. 60/003,418, filed Sep. 8, 1995.

BACKGROUND OF THE INVENTION

1. Field of the Invention

The present invention relates generally to the fields of drug action, cellular regulation and gene therapy. More specifically, the present invention relates to the novel finding that glucocorticoids enhance reporter gene activity when transfected by cationic lipid or liposomes.

2. Description of the Related Art

Human clinical trials for gene therapy as treatment of diseases caused by genetic defects or by gene dysregulation have shown promise and gained momentum in the last two years. Several diseases which manifest significant symptomology in the lung have been targeted for gene therapy, including cystic fibrosis and lung cancer. These trials have employed either recombinant retroviral or, adenoviral vectors as well as cationic lipids to transport and deliver the gene to the cell. Nonetheless, cellular transfer and subsequent gene expression is low and thus therapeutic levels of gene expression may be lacking. Moreover, immune responses developing against viral vectors may limit their use. While cationic lipids are less efficient at delivery than the adenoviral vectors, newer chemical designs have produced cationic lipids that are greatly improved over the original designs. Several animal and human trials have shown that, at cationic lipid concentrations typical for transfection, no negative side effects or immune response developed.

Delivery of gene therapy to the lung by aerosol allows genes to be delivered directly to the target tissue. Several groups have demonstrated aerosol delivery and transfection of animal lungs in vivo using reporter gene DNA coupled to cationic liposomes. The salient features noted in these studies were the absence of toxicity and a duration of gene expression of approximately 1 month. Gene expression was still relatively low; even modest transfection in mouse lungs required at least 0.5 to 12 milligrams of highly purified DNA. As reported, gene therapy by these methods would not be feasible for humans.

Another approach to increasing transfection efficiency is a greater understanding of plasmid uptake and the factors which influence expression of the transfected gene in the target tissue. In recent investigations as to the role of inflammation on gene transfection in lung cells, it was found that an exposure of A549 human lung carcinoma cells to the immune stimulator lipopolysacchride or the cytokine IL-1β before transfection with pCMVβgal-DMRIE/DOPE reduced the level of β-gal protein below that seen in the cells treated with medium only.

The prior art is deficient in the lack of effective means of delivering therapeutic levels of transfected genes. The present invention fulfills this longstanding need and desire in the art.

SUMMARY OF THE INVENTION

Little is known about: the mechanism by which cationic lipid-DNA complexes are taken up by the cell or, the fate of the complexes within the cell. Even less is known about factors in situ that may influence uptake, or the consistent delivery and expression of DNA once in the tissue, especially in patients with chronic lung inflammatory disease or any other immune process. The present invention demonstrates two findings which have a substantial effect on tranfection in cell culture and which have parallels in vivo. First, the present invention demonstrates that the cytokine IL-1β and the immune stimulator lipopolysacchride (LPS) suppress transfection/expression of pCMVβgal transfected into A549 human lung cancer cell lines or primary rat lung cells by cationic lipid. Secondly, anti-inflammatory topical glucocorticoids such as beclomethasone dipropionate (BEC) reverse the inhibitory effects of IL-1β and lipopolysacchride and even enhance expression of reporter genes above and beyond expression seen in untreated transfected cells, i.e., not treated with lipopolysacchride or IL1β, etc. The effect is specific to glucocorticoids, as opposed to other types of steroids but not to a particular glucocorticoid. This effect may also be specific to glucocorticoids as anti-inflammatory agents as this effect was not seen when cells were pre-treated with another immunosuppressant cyclosporine A. Glucocorticoid-mediated boost in transgene activity is independent of promoter, reporter gene and cationic lipid used. The mechanism by which glucocorticoids enhanced expression of reporter genes does not involve increased plasmid-lipid uptake, but rather an intracellular mechanism which does not involve new protein synthesis. In addition, pre-treatment of primary rat lung cells with synthetic topical glucocorticoids, in the absence of lipopolysacchride or IL-1β, prior to transfection enhanced the level of β-gal protein over untreated controls. The present invention describes studies concerning the mechanism of glucocorticoid-enhanced transfection of plasmid DNA. Thus, the present invention has direct relevance to the use of gene therapy in vivo.

In one embodiment of the present invention, there is provided a method of increasing the cellular expression of a gene in a biological tissue after delivery of said gene in an appropriate vector to an animal, comprising the step of: administering to said animal a pharmacologically effective dose of a glucocorticoid in an amount sufficient to increase the cellular expression of said gene.

In another embodiment of the present invention, there is provided a method of treating a pathophysiological state in a human by increasing the cellular expression of a gene in an appropriate vector after delivery of said gene into a biological tissue of a human in need of such treatment, comprising the step of: administering to said human a pharmacologically effective dose of a glucocorticoid in an amount sufficient to increase the cellular expression of said gene.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 2A shows the dose response of the transfected cells to beclomethasone, dose range from $10^{-7}$ to $10^{-6}$ M. FIG. 2B shows that several other topical glucocorticoids also induced enhanced β gal activity, at $10^{-6}$ M: Budesonide, BUD; Flunisolide, FLUN; Beclomethasone-dipropionate-dilauroyl Phosphatidylcholine, beclomethasone-DLPC. After treatment, cells were transfected with 1 μg/ml pCMVβgal- 4 μg of DMRIE/DOPE. β-gal activity was determined using the microtiter assay. Results represent the average and SD from 3 experiments. Fold-change=β-gal activity in glucocorticoid-treated cells/β-gal activity in medium-treated cells.

DETAILED DESCRIPTION OF THE INVENTION

Figure 1:
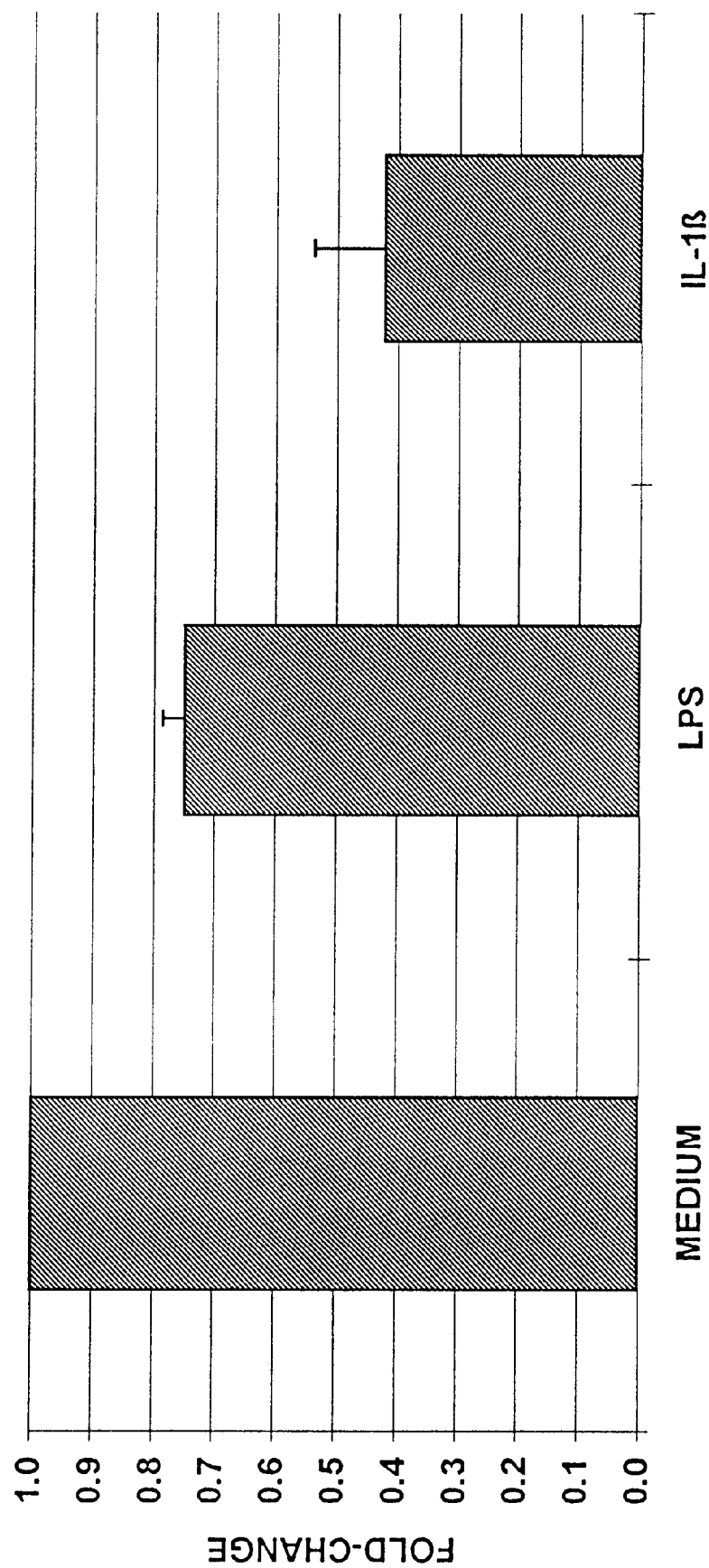
FIG. 1 shows that lipopolysaccharide and IL-1β suppress β-galactosidase (β-gal) activity in A549 cells transfected with pCMVβgal-cationic lipid. A549 cells were treated with either medium, 0.5 μg/ml of lipopolysaccharide or 100 U/ml recombinant human IL-1-β for 4 hours. After treatment, cells were transfected with 1 μg/ml pCMVβ-gal- 4 μg of DMRIE/DOPE. β-gal activity was determined using a (CPRG) colorimetric microtiter assay specifically measuring βgalactosidase activity. Results represent the average and standard deviation from 3 experiments. Fold-change=β-gal activity in lipopolysaccharide or IL-1 samples/β-gal activity in medium-treated samples.

In the present invention, the following abbreviations may be used: lipopolysacchride: *Salmonella typhimurium* lipopolysacchride; IL-1β: Interleukin-1β; GC: glucocorticoids; E2: estradiol; PROG: progesterone; CHOL: cholesterol; BUD: Budesonide; BEC: beclomethasone dipropionate; FLUN: flunisolide; DLPC: dilauroyl phosphatidylchoine; β-gal: *Escherichia coli* beta-galactosidase; CAT: chloramphicol acetyl transferase; DMRIE/DOPE: N-(2-hydroxyethyl)-N,N-dimethyl-2,3-bis (tetradecytoxy)-1-propanaminium bromide dioleoyl phosphatidylethanolamine; DOSPA/DOPE: 2,3 dioleyloxy-N-[2 (sperminecarboxamido)ethyl]-N,N dimethyl-1-propanaminium trifluoroacetate: dioleoyl phosphatidylethanolamine; DMEM: Dulbecco's minimal essential medium; FBS: fetal bovine serum; CHX: cycloheximide; RS-PCR: RNA-specific polymerase chain reaction; CPRG: Chlorophenored-β-D-galactopyranoside; cAMP: cyclic adenosine monophosphate; CREB: cAMP responsive element binding protein;

The present invention is directed to a method of increasing the cellular expression of a gene in a cell after delivery of said gene to an animal, comprising the step of: administering to said animal a pharmacologically effective dose of a glucocorticoid in an amount sufficient to increase the cellular expression of said gene.

The present invention is also directed to a method of treating a pathophysiological state in a human by increasing the cellular expression of a gene after delivery of said gene into a biological tissue of an animal in need of such treatment, comprising the step of: administering to said animal a pharmacologically effective dose of a glucocorticoid in an amount sufficient to increase the cellular expression of said gene.

Generally, any glucocorticoid may be used in the method of the present invention but apparently not any anti-inflammatory since the effect was not seen in cyclosporine A-treated cells. Representative examples of useful glucocorticoids include hydrocortisone, prednisone, prednisolone, triamcinolone, betamethasone, budesonide, flunisolide and dexamethasone. The glucocorticoids may be either synthetic or non-synthetic glucorcorticoids. Generally, the glucocorticoid is administered in a dose of from about 0.6 mg/kg to about 50 mg/kg, dependent upon which glucocorticoid, as a diffence in potency exists and, whether a physiologic or pharmacologic dose is to be delivered. In the methods of the present invention, the glucocorticoid may be in either a lipid soluble form, an ethanol soluble form or a water soluble form, any of which may be incorporated into a liposome.

Generally, the glucocorticoid may be administered in a fashion that optimzes the ability of the glucocorticoid to enhance the activity of the gene delivered. For example, the glucocorticoid may be administered concurrently with the delivery of said gene, prior to delivery of said gene or after delivery of said gene. The route of administration may be any that is desirable in the art including aerosol, intravenous, intraperitoneal, etc.

The methods of the present invention are efficacious regardless of the biological tissue to which the gene is delivered. For example, the activity of a gene may be enhanced if it is delivered to tissues such as the liver, leukocytes, lung, gastrointestinal tract, kidney, skeletal muscle, smooth muscle, neurological tissue, skin cells, cancer cells, eye, bone marrow and tumors.

The delivery of the gene may be by any route. For example, the gene may be delivered by injection, oral administration dermal or aerosol administration. In another embodiment, the glucocorticoid may be encapsulated in a liposome, neutral or charged as is well known in the art. Alternatively, the gene may be dissolved in a solvent such as ethanol.

The methods of the present invention are efficacious in any animal, either human or non-human. That is, although the methods of the present invention have primary utility in humans various veterinary uses will be apparent to those having ordinary skill in this art.

In the methods of the present invention, the gene may be transfected by a known method. Representative examples of methods of transfecting a gene into a biological tissue include viral transfection, cationic lipid transfection, and targeted gene therapy utilizing a receptor and a cationic amine such as poly-L-lysine. In fact, any gene's activity may be enhanced using the instant methodology whether a recombinant gene, a native gene, a cDNA or an oligomer. The glucocorticoid enhances the activity of a vector at the promoter or at some cell regulatory step prior to translation.

The following examples are given for the purpose of illustrating various embodiments of the invention and are not meant to limit the present invention in any fashion.

EXAMPLE 1

Cells and Cell Culture

A549 were obtained from ATCC. A549 were maintained in Dulbecco's minimal essential medium (DMEM, GIBCO-Life Technologies) plus 10% low lipopolysacchride-containing, defined fetal bovine serum (FBS, Hyclone), 200 mM L-glutamine and 50 μg/ml of Gentamicin. For most transfections, cells were plated at $3\times10^4$ cells/ml in 12 well cluster dishes (Corning). This concentration of cells provides a monolayer approximately 30% confluent at 24 hours post cell transfer.

Primary rat lung cells: were prepared as follows. Lungs were harvested from adult Sprague-Dawley female rats and finely minced. The minced lung was resuspended in a solution of 0.5×trypsin in Hank's balanced salt: solution for 1 hour and then a solution containing 100 U/ml of collagenase (C. perfringens, IV, Sigma Chemical), 100 U/ml DNase I (Sigma), in Dulbecco's minimum essential medium (DMEM) with 10% fetal bovine serum (FBS). Tissue was incubated on a rocker at 37° C. for 1.5 hours. Dissociated cells were filtered through several layers of sterile gauze and plated in 6 well cluster dishes (Corning) at $1.0\times10^6$ cells/well in DMEM+10% FBS. Cells were incubated in a humidified 37° C. 5% $CO_2$ incubator for 13–24 hours prior to transfection.

EXAMPLE 2

Chemicals and Reagents

Cycloheximide, lipopolysaccharide (lipopolysacchride, *S. Typhimurium*). Budesonide (BUD) and flunisolide (FLU) were also purchased from Sigma Chemical Co. St. Louis, Mo. All glucocorticoids were dissolved in absolute ethanol. Beclomethasone dipropionate was the gift of Orion Pharmaceuticals, Kuopio, Finland. Beclomethasone, in a neutral liposome, dilauroyl phosphatidylcholine (DLPC, Avanti Polar Lipids, Birmingham, Ala.) was made by dissolving 0.5 mg of beclomethasone and 25 mg of DLPC in tertiary butanol at 37° C. Samples were then flash frozen in ethanol and dry ice and lyophilized. Liposomes were reconstituted in sterile, endotoxin-free water. Human recombinant IL-1β was purchased from Genzyme Corp. (Cambridge, Mass.).

EXAMPLE 3 cDNA pCMVβgal and pCMVHICAT were obtained from Genzyme Corp. and pSVβ was purchased from Clontech (CA).

Plasmid DNA was extracted and purified using the Qiagen column purification system (Qiagen, Chatsworth, Calif.). Most of the lipopolysacchride was removed from the plasmid preparation the use of a E-TOX column (Sterogene, Calif.). Plasmid was evaluated for endotoxin using the LAL kit from Biowhitaker/Microbiological Associates (Bethesda, Md.). DNA concentration was determined by $A_{260}$ reading and comparing similar concentrations of plasmid-purified DNA with $CsCl_2$-purified DNA. One OD unit of absorbance at 260 nm is equal to 50 μg/ml of DNA.

EXAMPLE 4

Lipids 2,3 dioleyloxy-N-[2(sperminecarboxamido)ethyl]-N,N dimethyl-1-propanaminium trifluoroacetate (DOSPA), dioleoyl phosphatidylethanolamine (DOPE) (DOSPA/DOPE, Lipofectamine) was purchased from GIBCO/BRL. N-(2-hydroxyethyl)-N,N-dimethyl-2,3-bis(tetradecytoxy)-1-propanaminium bromide (DMRIE)/DOPE was obtained from Genzyme Corp. (Framingham, Mass.).

EXAMPLE 5

DNA-Cationic Liposome Preparation

DNA-lipid ratio was optimized as follows. Plasmid cDNA (2.5 μg) was combined with various concentrations of cationic lipid in water to generate a panel of DNA:lipid ratios. DNA-lipid mixtures were allowed to incubate for 15 minutes at room temperature and the complexes were resolved by electrophoresis on a 1% agarose gel in 1× Tris-acetate (40 mM)-EDTA (2 mM) (TAE) buffer. Optimal ratios were considered the concentration of DNA:lipid where all DNA was bound by lipid and therefore retained at the gel origin. Ratios were confirmed by transfection of A549 cells as described below. Optimal DNA:lipid ratios were confirmed for each lipid and plasmid combination and, between each batch of DNA and lipid. For DOSPA/DOPE the optimal DNA:lipid ratio by weight was 1 μg DNA: 3 μg of lipid and for the DMRIE/DOPE, 1 μg DNA: 4 μg lipid.

EXAMPLE 6

Transfection

All transfections were performed in OPTIMEM (GIBCO-Life Technologies). One μg of pCMVβ gal was combined with 4 μg of DMRIE/DOPE or 3 μg of DOSPA/DOPE in 1 ml of OPTIMEM and incubated for 15 minutes at room temperature. Cell monolayers were washed twice in serum-free medium then overlaid with 1 ml of transfection mixture and incubated for 2.5 hours at 37° C. in a humidified, 5% $CO_2$. DNA-liposome overlay was replaced with DMEM plus 10% FBS and cells were incubated for 48 hours. Cell lysates were harvested and assayed for total protein according to the manufacturer's instructions (BCA assay, Pierce Chemical, Rockfield, Ill.) and β-galactosidase activity was determined using a Chlorophenored-β-D-galactopyranoside colorimetric microtiter assay as described (CPRG) assay (Boerhinger-Mannheim, Germany). Where specified, cell monolayers were washed with PBS then fixed with 2% formaldehyde-0.2% glutaraldehyde and stained with X-gal (40 μg/ml, 5'–3' Inc. Boulder, Colo.) in 20 mM potassium ferricyanide, 20 mM potassium ferrocyanide and 2 mM magnesium chloride.

EXAMPLE 7

DNA-Lipid Uptake Studies $^3$H-thymidine-labeled pCMVβgal plasmid was prepared by adding 1 mCi of $^3$H-TdR ($^3$H-TdR, 74GBq/mmol, Amersham) to a 25 ml overnight culture of pCMVβgal-transformed DH5α strain of *Escherichia coli*. Labeled plasmid was isolated using Qiagen tip columns (100 μg size, Chatsworth, Calif.) per manufacturer's instructions. Saturable binding of the labeled DNA was determined as follows. Serial dilutions, from 1 μg–0.125 μg of $^3$-H-TdR-labeled DNA was added to A549 cells and incubated for either 2, 6 or 24 hours. Monolayers were washed, rinsed with 1× trypsin, lightly trypsinized and cells pelleted by centrifugation. Pellets were lysed in 100 μl of lysis buffer (0.1 M TRIS and 0.5% Triton X-100), liquid scintillation cocktail added (BCS, Amersham) and $^3$H-plasmid label quantitated by liquid scintillation. For uptake experiments, A549 cells were pretreated with either glucocorticoids or medium for 4 hours. Cells were treated with the saturable concentration of $^3$-H-labeled plasmid plus lipid for 2.5 hours. Uptake was determined as described above.

EXAMPLE 8

RNA-specific PCR (RS-PCR)

RS-PCR was performed as described and is well known in the art. Briefly, cells were pre-treated with beclomethasone at $10^{-6}$ M and transfected as described above. After the incubation was complete, cells were lysed using acidified guanidinium isothiocyante (Fluka Chemical), containing 0.75 M sodium citrate and 1% sarkosyl. RNA was harvested using the RNAeasy system (Qiagen, Chatsworth, Calif.). Total RNA quantity was determined by $A_{260}$ and, 0.5 μg of the RNA was run on a gel to determine RNA integrity. Using 0.3 μg of total RNA, cDNAs were prepared using MMLV reverse transcriptase (GIBCO, Life Technologies), substituting primer T30D20-gal (GAACATCGATGACAAGCTTAGGTATCGATACACC TCG CGGAAACCGACAT) (SEQ ID NO: 1) for oligo dT. This primer contains 20 base pairs complementary to the 3' end of the mRNA and 30 irrelevant bases. In addition, each reaction was spiked with 2.5 μCi of $^{32}$-P α-dCTP as a tracer. Reactions were incubated at 37° C. for 1 hours. When incubation was complete, DNA-RNA hybrids were harvested using the Qiaquick spin PCR purification kit (Qiagen, Chatsworth, Calif.) to remove primer and unincorporated isotope. One μl of cDNA was spotted to duplicate nitrocellulose filters and counted by LSC.

For PCR, 25,000 CPM were used for each sample. PCR was otherwise performed as described. The PCR cocktail contained 500 mM KCl, 50 mM TRIS-HCl, pH 9.0,50 mM NaCl, 10 mM $MgCl_2$, 200 μM dNTPS and 1 Unit Taq DNA Polymerase (Promega, Madison Wis.). Primers: 5βgal (GAGAATCCGACGGGTTGTTACT) (SEQ ID NO: 2) and T30-gal (GAACATCGATGAACAAGCTYAGGTATCGATA) (SEQ ID NO: 3), which represents the terminal 30 nucleotides of the T30D20-gal oligomer, were used at a concentration of 1.25 μM. PCR cycling was optimized for this combination of primers and templates (33 cycles). Upon completion of PCR, products were resolved on a 1% TAE agarose gel, then blotted to nylon filter. Filters were hybridized with $^{32}$P-labeled pCMVβgal probe overnight and washed to remove non-hybridized counts. Blots were evaluated on a Betagen betascanner and CPM for bands of the correct size were determined.

EXAMPLE 9

Effect of Bacterial Lipopolysacchride and Interleukin-1-β on Transfection Efficiency Lipopolysacchride in the bacterial cell is a potent immunomodulator, capable of triggering a cascade of events including cytokine production and cellular recruitment. In previous studies, A549 cells were shown to respond to both lipopolysaccharide and IL-1-β by upregulation of IL:-1β mRNA (lipopolysaccharide) as well as the induction of IL-8 mRNA (IL-1β).

In the present invention, A549 cells were treated with either 100 U/ml IL-1β or 0.5 μg/ml lipopolysaccharide for 4 hours, then transfected with pCMVβgal-DMRIE/DOPE. As can be seen in FIG. 1, both IL-1β and lipopolysaccharide decreased β-gal activity significantly, relative to the medium treated A549 cells.

EXAMPLE 10

Figure 2A:
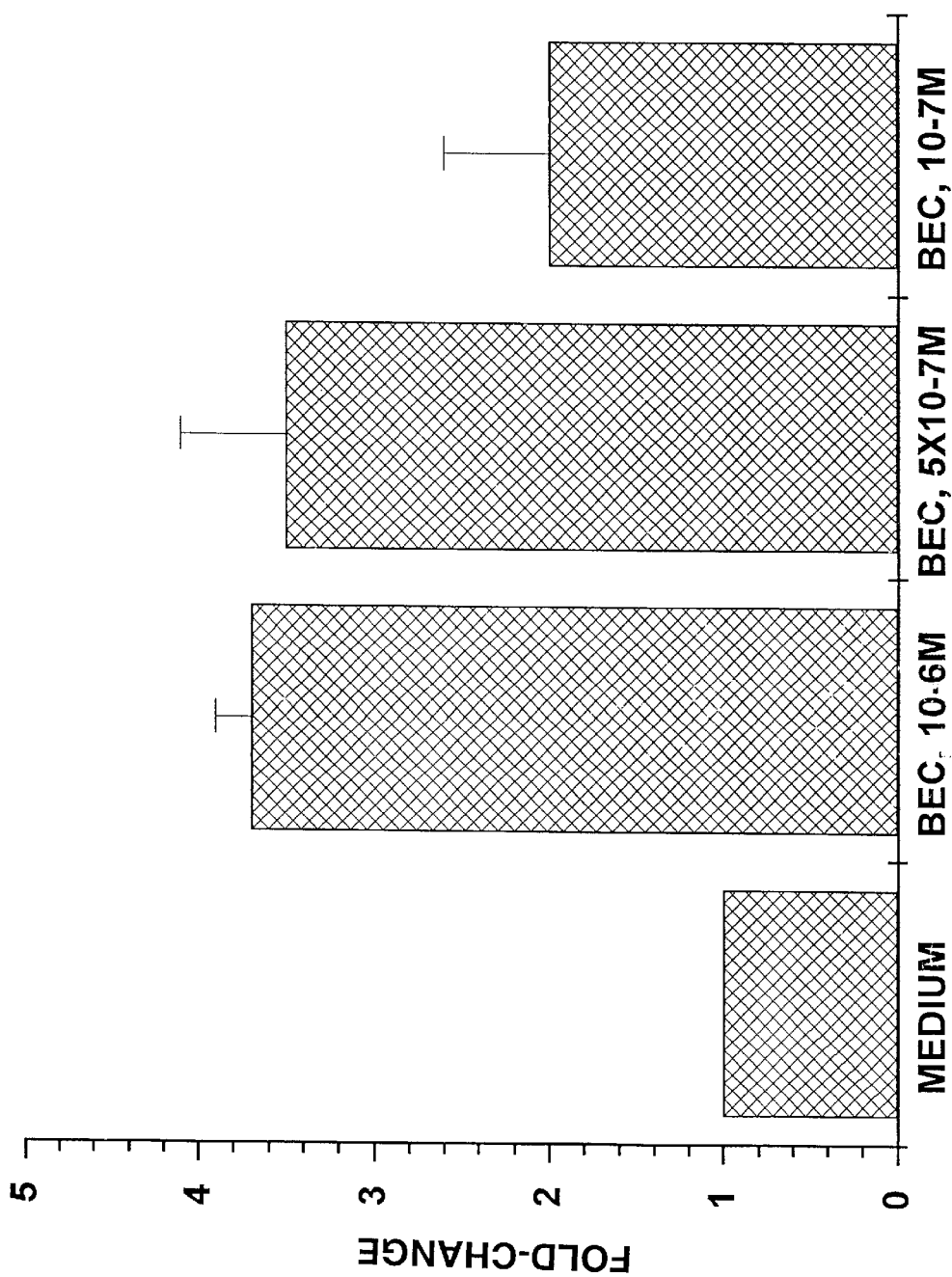
FIGS. 2A–2B show that glucocorticoids enhance β-gal activity in transfected A549 cells. A549 cells were treated for 4 hours with glucocorticoids.
Figure 2B:
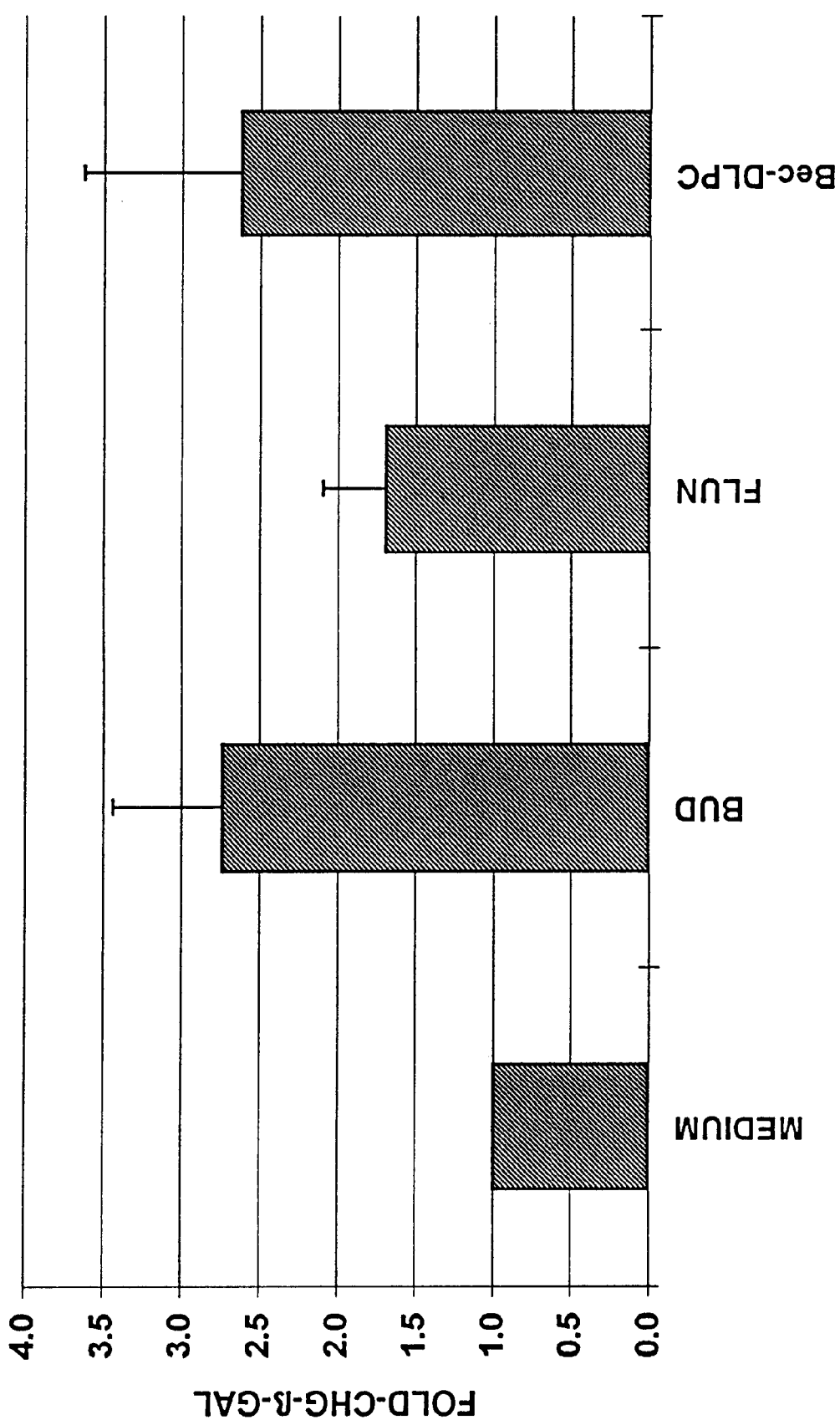

Topical Glucocorticoids Enhanced β-Galactosidase Activity in pCMVβgal-Cationic Lipid-transfected in A549 Cells A549 cells were pre-treated with synthetic, topical glucocorticoid beclomethasone, in a dose range between $10^{-7}$–$10^{-6}$ M or medium for 4 hours prior to transfection. Enhancement of 2–4 fold was consistently seen with beclomethasone in the range $5\times10^{-7}$ M to $10^{-6}$ M, with only slight enhancement seen at $10^{-7}$ M (FIG. 2A). In addition, other topical steroids such as budesonide, FLUN and a neutral liposomal form of beclomethasone, beclomethasone-DLPC, also enhanced β-gal activity in A549 cells (FIG. 2b). Beclomethasone-DLPC, at $10^{-6}$ M also enhanced β-gal activity to a similar degree as budesonide or beclomethasone in ethanol (FIG. 2A), which showed that the liposome moiety did not interfere with this effect. The FLUN consistently demonstrated less of an enhancing effect, which is consistent with the potency of the glucocorticoids.

EXAMPLE 11

Glucocorticoid-treatment Reverses the Suppression of Gene Expression by IL-1-β and Lipopolysaccharide Beclomethasone appeared to have reversed the undesirable effects of these two immunomodulators. To demonstrate this phenomenon more particularly, A549 cells were pretreated with $10^{-6}$ M beclomethasone for 4 hours, followed by a treatment with lipopolysaccharide or IL-1-β for 4 hours prior to transfection with pCMVβgal-DMRIE/DOPE. As seen previously, the IL-1β and lipopolysaccharide suppressed the degree of β-gal expression and the beclomethasone enhanced β-gal activity by 2.5-fold. In cells, pretreated with beclomethasone, then treated with either IL-1β or lipopolysaccharide (beclomethasone, lipopolysaccharide; beclomethasone, IL-1β), β-gal expression exceeded that seen in untreated cells by 2-fold and approached the level of the "beclomethasone only" pre-treated cells, suggesting that the beclomethasone blocked the inhibitory effects of IL-1β or lipopolysaccharide.

Since many of the patients targeted for gene therapy may have chronic gram negative bacterial infections, the inhibitory effects of the lipopolysaccharide and IL-1β would most probably be in place before delivery of the gene or the beclomethasone. To determine whether or not the enhancing effect of the beclomethasone on β-gal expression could overcome the suppression of βgal activity in lipopolysacchride or IL-1β pretreated cells, A549 cells were pre-treated for 4 hours with lipopolysaccharide or IL-1β, then treated for 4 hours with beclomethasone prior to transfection with pCMVβgal-DMRIE/DOPE (1β, BEC; lipopolysaccharide, BEC).

Figure 3:
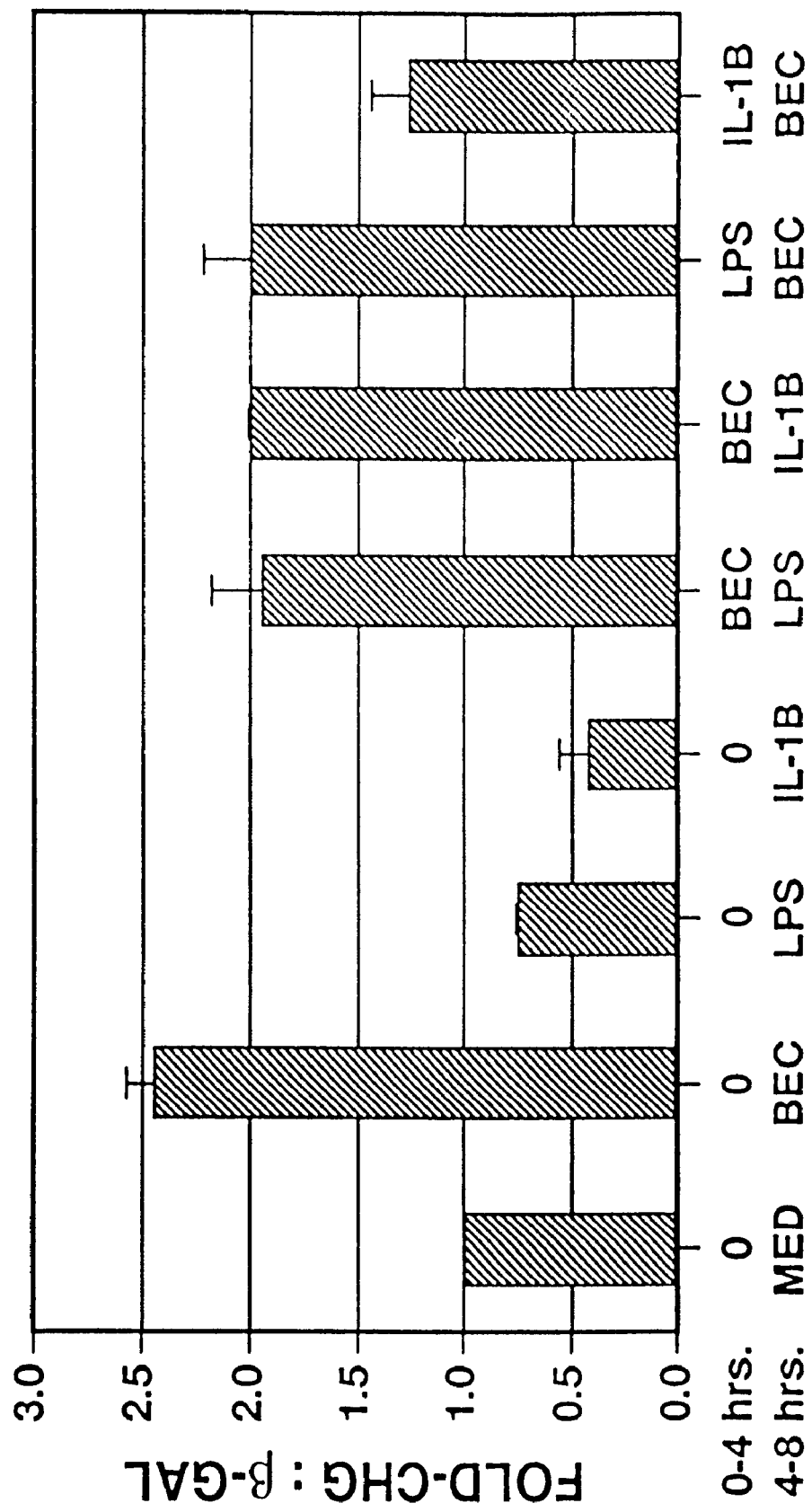
FIG. 3 shows that beclomethasone reverses the inhibitory effect of lipopolysaccharide and IL-1β on β-gal activity in transfected A549 cells. A549 cells were treated for 4 hours with medium only, beclomethasone ($10^{-6}$ M), IL-1β (100 U/ml) or lipopolysaccharide (0.5 μg/ml). After the first 4 hours, supernatant was removed and cells were treated with either, medium, IL-1β, lipopolysaccharide or beclomethasone, as designated an additional 4 hours (i.e., beclomethasone, lipopolysaccharide; beclomethasone for first 4 hours, lipopolysaccharide for the second 4 hours). After the second treatment, cells were transfected with 1 μg/ml pCMVβgal- 4 μg of DMRIE/DOPE. βgal activity was determined using the microtiter assay. Results shown represent the average and SD from 2 experiments. Fold-change=β-gal activity in beclomethasone, lipopolysaccharide, IL-1 or combination treated cells/β-gal activity in medium treated cells.

FIG. 3 shows that even when cells were treated with lipopolysaccharide or IL-1β, such that the inhibitory process is already established (see lipopolysaccharide, IL-1β only), beclomethasone dipropionate treatment not only restored βgal activity, but still augmented βgal activity above what was seen in medium treated, transfected cells. The level of β-gal activity in the lipopolysaccharide or IL-β pretreated, then beclomethasone-treated cells did not quite achieve the level of enhanced β-gal activity seen in cells pre-treated with beclomethasone only, suggesting that some aspect of lipopolysaccharide or IL-β-induced inhibitory activity remained. Thus, the present invention demonstrates that, even during existing infections, beclomethasone treatment improves gene transfection by DNA-cationic lipid.

EXAMPLE 12

Figure 4:
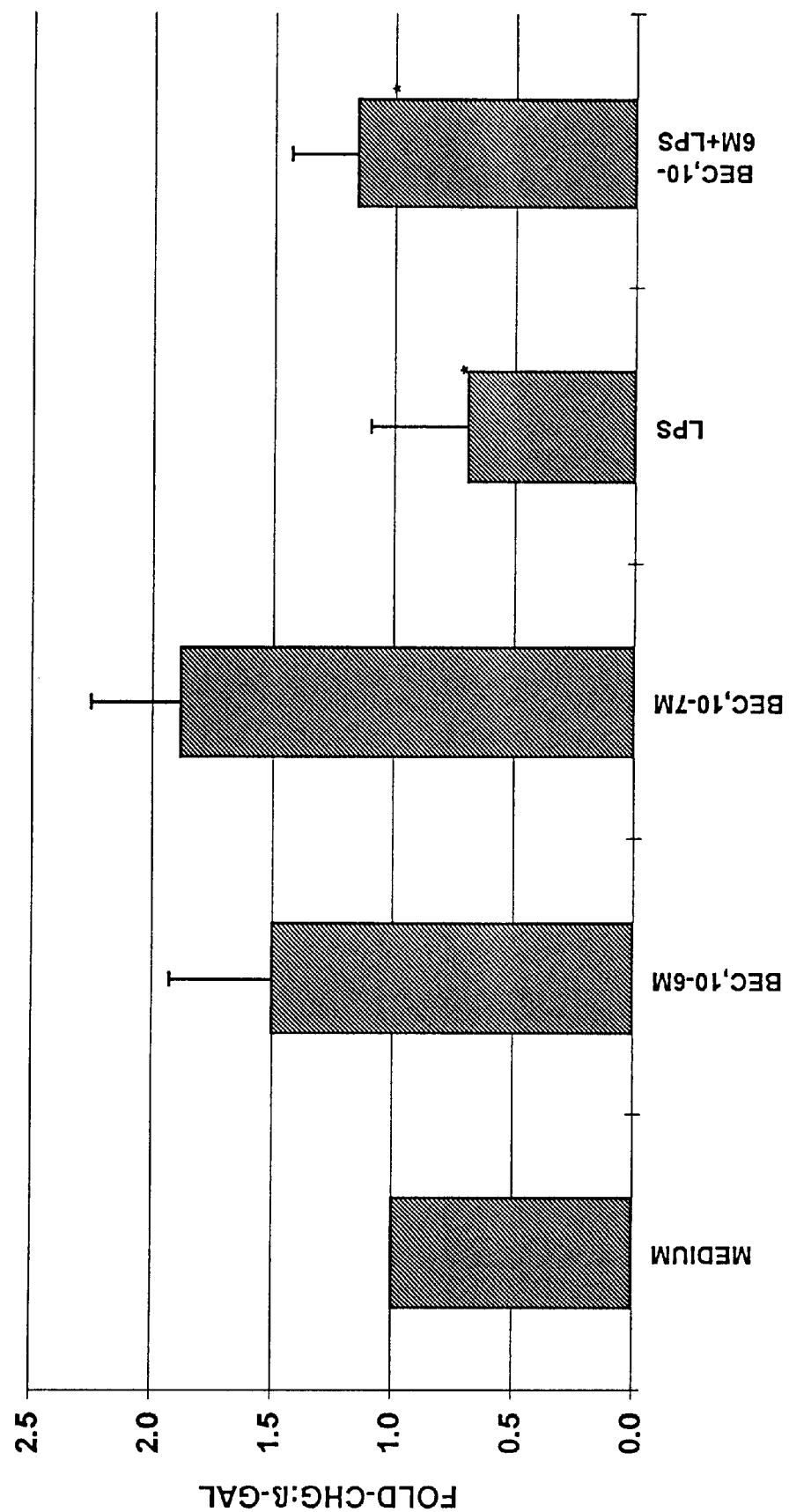
FIG. 4 shows that beclomethasone enhances β-gal activity in primary rat lung cells. Primary rat lung cells were isolated from enzymatically digested rat lungs and plated at 1.0×10⁵ cells/well in cell well tissue culture dishes. Cells were pretreated with beclomethasone, lipopolysaccharide (0.5 μg/ml) or beclomethasone+lipopolysaccharide (4 hours beclomethasone+4 hours lipopolysaccharide) in a concentration range of $10^{-7}$–$10^{-6}$ M for 4 hours then transfected with 3 μg of DNA and 12 μg of DMRIE/DOPE. At 48 hours, β-gal activity was determined by CPRG microtiter assay. Results represent the average and SD from 3 (*2) experiments. Fold-change=β-gal activity in beclomethasone, lipopolysaccharide, beclomethasone+lipopolysacchride-treated-cells/βgal activity in medium-treated cells.

Characterization of Glucocorticoid-mediated Enhancement of Reporter Gene Activity To determine whether or not the enhancement of βgal activity by glucocorticoids was a more generalized phenomenon, primary rat lung cells were isolated and pre-treated with either medium or glucocorticoids for 4 hours prior to transfection with pCMVβgal-DMRIE/DOPE. As can be seen in FIG. 4, a composite of results from several different preparations of rat cells, a 2-fold enhancement of β-gal activity was seen. Primary rat lung cells appeared to be more sensitive to beclomethasone, than were the A549 cells, with the optimum enhancement in βgal activity found at $10^{-7}$ M. Similar to what was observed in A549 cells, lipopolysaccharide-suppressed βgal activity. Also, beclomethasone pretreatment, followed by lipopolysaccharide stimulation, restored βgal activity to that of the medium pre-treated cells; enhancement above the control was slight. Thus, glucocorticoids also reversed the inhibitory effects of lipopolysaccharide on β-gal activity in a heterogeneous population of primary rat lung cells, suggesting that glucocorticoids may also enhance transfection of similar cell types in vivo.

Figure 5A:
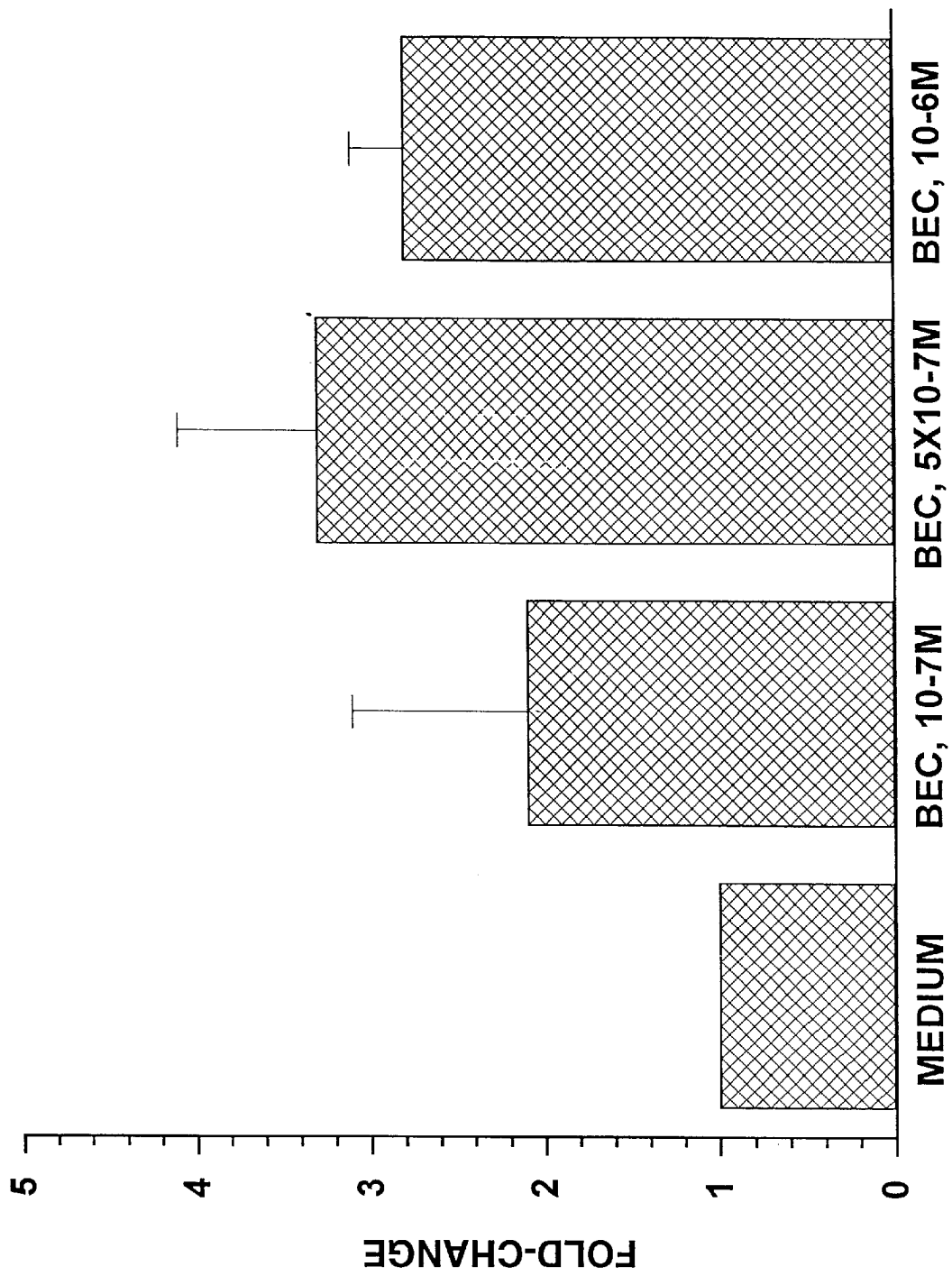
FIGS. 5A–5C show that the beclomethasone-mediated enhancement is not limited cationic lipid, vector promoter or vector reporter genes and is specific to glucocorticoids. A549 cells were treated for 4 hours with beclomethasone or other steroids (FIG. 5B, steroids: estrogen, E2; Progesterone, PROG; Cholesterol, CHOL). After treatment, cells were transfected; with, in FIG. 5A, 1 μg/ml pCMVβgal and 3 μg/ml DOSPA/DOPE, in FIG. 5B, 1 μg/ml pSVβ and 4 βg/ml DMRIE/DOPE or 1 μg/ml pCMVβ-gal and 4 μg/ml DMRIE and FIG. 5C, 1 μg/ml pCMVHICAT and 4 μg/ml DMRIE/DOPE. βgal activity was determined using the microtiter assay. Chloramphicol acetyl transferase (CAT) activity was determined by TLC chloramphicol acetyl transferase assay where isotope $^{14}$C acetylated forms of chloramphenicol were resolved by TLC and $^{14}$C -incorporation determined by betascanner set to detect $^{14}$C. Results in FIG. 5A and FIG. 5C represent the average and SD from 3 experiments. Results in FIG. 5B are representative of 3 experiments. Fold-change=βgal or CAT activity in beclomethasone or steroid-treated cells/βgal or chloramphicol acetyl transferase activity in medium treated cells.
Figure 5B:
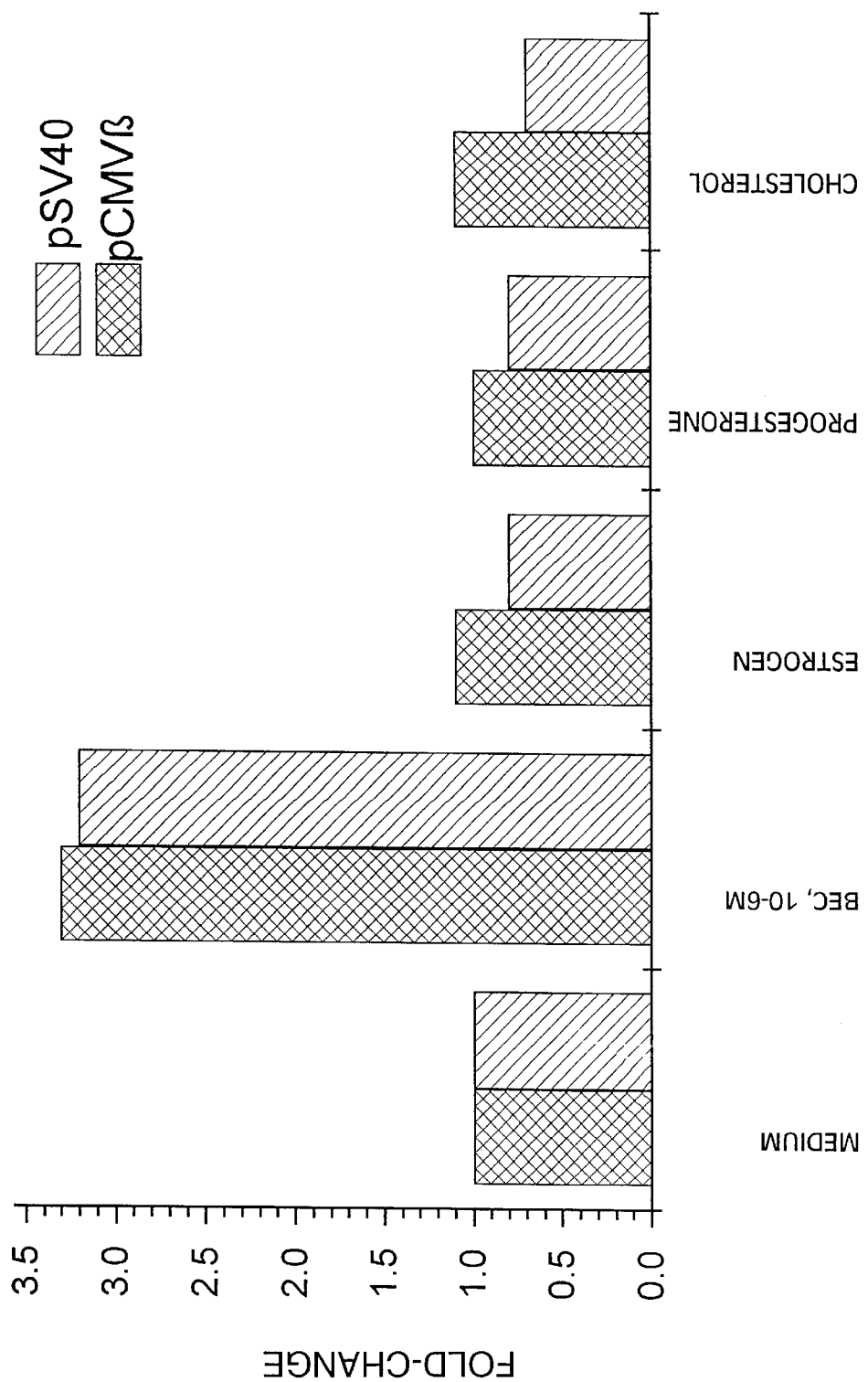
Figure 5C:
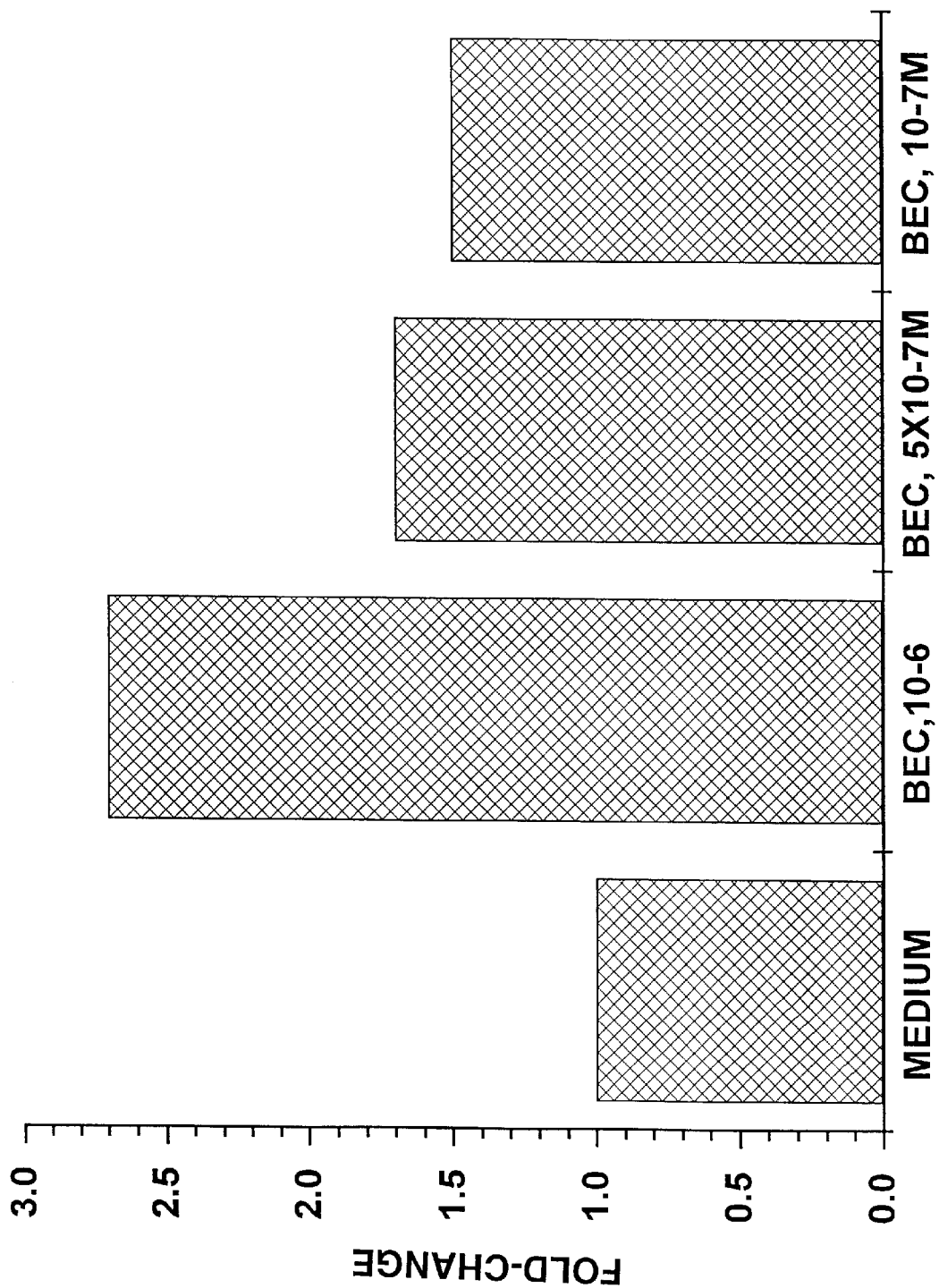

The glucocorticoid effect was not specific to cationic lipid, DMRIE/DOPE, as β-gal expression was also enhanced in cells pre-treated with beclomethasone then transfected with pCMVβgal-and DOSPA/DOPE, another cationic lipid (FIG. 5A). Moreover, the effect was not specific to the CMV promoter in the vector as the glucocorticoid-mediated enhancement was observed when A549 cells were pre-treated with beclomethasone dipropionate and transfected with pSVβ-DMRIE/DOPE, a vector that contains the SV40 promoter (FIG. 5B). Finally, the glucocorticoid-mediated enhancement of gene expression was not limited to the reporter gene β-gal as similar results were seen when the reporter gene was chloramphenicol acetyl transferase (CAT) (FIG. 5C).

To rule out the possibility that other steroids might also augment βgal activity, A549 cells were treated with various doses of either estrogen (estradiol), progesterone, cholesterol or beclomethasone for 4 hours prior to transfection with either pCMVβ gal or pSVβ using cationic lipid DMRIE/DOPE. Enhancement of β-gal was only seen in the beclomethasone treated cells, showing that, in A549, the enhancing effect was glucocorticoid-specific (FIG. 5B). The dose response of the beclomethasone-mediated enhancement using an alternate lipid, promoter or reporter was similar to that seen with pCMVβgal plus DMRIE/DOPE in A549 cells, with $5\times10^{-7}$ to $10^{-6}$ M producing maximal enhanced reporter gene activity.

These combined results of the studies of the present invention demonstrate that this effect related to glucocorticoid action on cells was a general phenomenon and was not specific to a particular glucocorticoid, reporter gene, promoter, lipid, or cell line. The effect was dose-dependent in primary lung cells demonstrating a greater sensitivity to the beclomethasone. Since the effect was not specific to particular glucocorticoids, beclomethasone dissolved in ethanol was used for the remainder of the studies described herein.

EXAMPLE 13

Mechanism of Beclomethasone Dipropionate-mediated Enhancement of Reporter Gene Expression Vector Uptake One possibility for enhanced reporter gene expression was increased uptake of vector. This possibility was addressed in two ways: determining the number of β-gal stained cells vs. activity and, radiolabeled-plasmid-cationic lipid uptake.

For stained cells, duplicate cell cultures of A549 cells were treated for 4 hours with beclomethasone dipropionate or medium only, then transfected with pCMVβgal using DMRIE/DOPE. At 48 hours, one set of cultures was lysed and βgal activity determined while the other set was fixed with neutral buffered formalin and stained with β-gal (duplicate wells for each treatment). Stained cells were counted in a 1×1 cm$^2$ area. As can be seen in TABLE I, while β-gal activity was increased in the β-gal assay, the number of cells stained for β-gal was similar between the medium-pretreated cells and the beclomethasone dipropionate pre-treated cells, suggesting that the enhanced β-gal expression was not due to a greater number of cells taking up plasmid.

TABLE I

| TREATMENT | FOLD-CHANGE, X-GAL STAINING | FOLD-CHANGE, βGAL ACTIVITY |
|---|---|---|
| DNA-DMRIE/DOPE | 1 | 1 |
| BEC, 10$^{-6}$ M, DNA-DMRIE/DOPE | 1.5 ± 0.7 | 3 |

Figure 6:
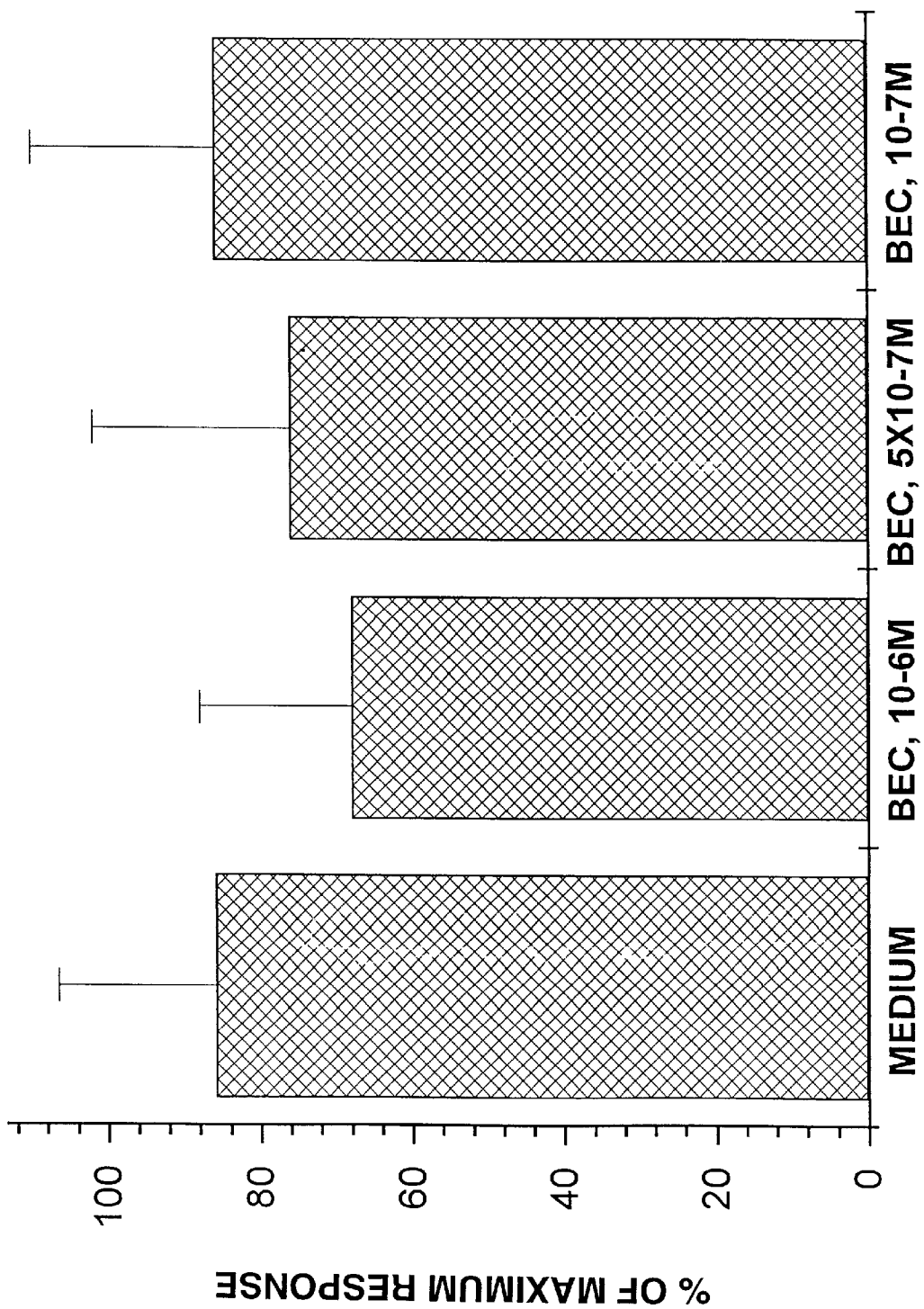
FIG. 6 shows that beclomethasone does not increase plasmid uptake in A549 cells. A549 cells were pretreated with medium or beclomethasone at the dose specified for 4 hours, then transfected with $^3$H-thymidine-labeled pCMVβgal. Two hours post-transfection, cells were washed, lightly trypsinized and pelleted by centrifugation. Pellets were then lysed, resuspended, and liquid scintillation cocktail added. $^3$H-thymidine-labeled pCMVβgal uptake (CPM) per sample was determined. Results represent the average and standard deviation from 4 experiments and each experimental point was performed in duplicate. Fold-change= CPM beclomethasone-pretreated/CPM medium pretreated.

Since it was possible that the staining technique was not sensitive enough to allow detection of increased plasmid uptake, this question was approached by comparing uptake of radiolabeled plasmid in beclomethasone-treated or medium-treated cells. To assure that the plasmid was basically unaltered by the labeling, the plasmid was metabolically labeled by adding $^3$H-thymidine to the bacterial culture during plasmid preparation (vide supra). After determining saturable binding and kinetics of uptake for the labeled material, A549 cells were treated for 4 hours with several concentrations of beclomethasone dipropionate, then transfected with $^3$ H-labeled DNA-DMRIE/DOPE. At 2 hours, cells were trypsinized, lysed and uptake of radiolabeled plasmid determined by LSC. The results presented in FIG. 6 confirm what was seen by staining; beclomethasone does not appear to enhance uptake, and thus, beclomethasone must function to enhance β-gal activity by some other mechanism.

EXAMPLE 14

Kinetics of GC-mediated Enhancement of Transfected D-gal Expression

Figure 7:
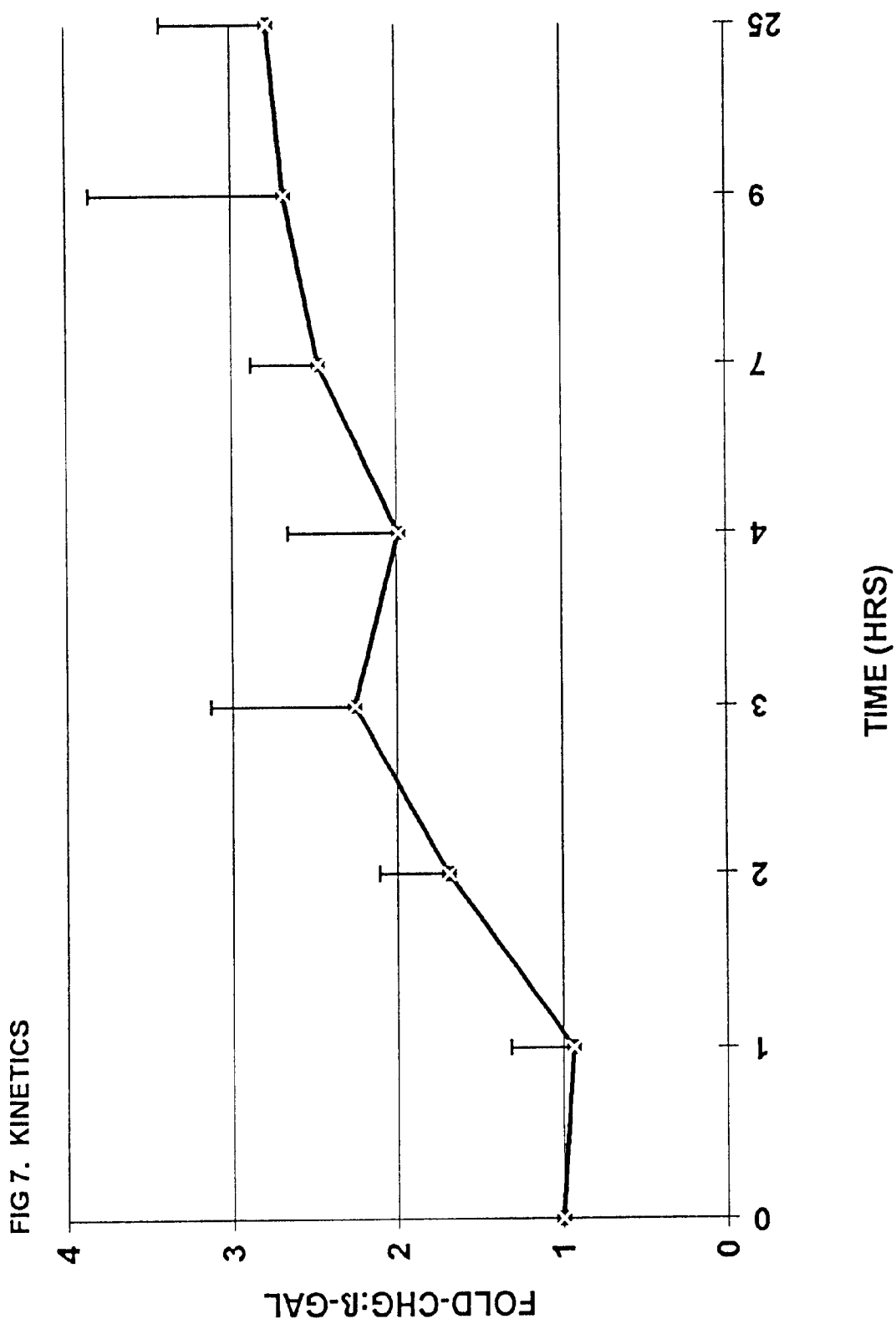
FIG. 7 shows the kinetics of beclomethasone-enhanced reporter gene expression. A549 cells were treated for various times with $10^{-6}$ M beclomethasone or medium. Cells were transfected cells were transfected with 1 μg/ml pCMVβgal- 4 μg of DMRIE/DOPE. βgal activity was determined using a CPRG microtiter assay. Results represent the average and SD from 2 experiments. Fold-change=β-gal activity in beclomethasone-treated cells/βgal activity in medium-treated cells.

To define the time course by which glucocorticoid-induced enhancement of βgal activity, A549 cells were pre-treated for various timed periods with either medium or 10$^{-6}$ M beclomethasone to determine kinetics of this effect. As can be seen in FIG. 7, a minimum of 3–4 hours of beclomethasone exposure was required in order to see the enhanced β-gal transfection. Enhanced β-gal activity was maximized by 8 hours pre-treatment and remained maximal for the 24 hours monitored. The 3–4 hours pre-incubation requirement plus, the plasmid uptake experiments suggest that an intracellular synthetic step may be involved in mediating the beclomethasone enhanced β-gal response rather than a cell surface event.

EXAMPLE 15

Intracellular Action of Glucocorticoid-mediated Enhancement of Vector Activity

To demonstrate whether or not beclomethasone-mediated enhancement of β-gal activity required protein synthesis, the protein synthesis inhibitor cycloheximide (CHX) was employed. Designated A549 cell cultures were pre-treated with medium or CHX to impose a block in protein synthesis. After 30 minutes, medium-treated cell cultures were treated with either medium or beclomethasone. Those already CHX-treated, were additionally treated with either med+CHX or beclomethasone+CHX for 4 hours. All cells were transfected with pCMVβgal-DMRIE/DOPE and β-gal activity was determined 48 hours later.

Figure 8:
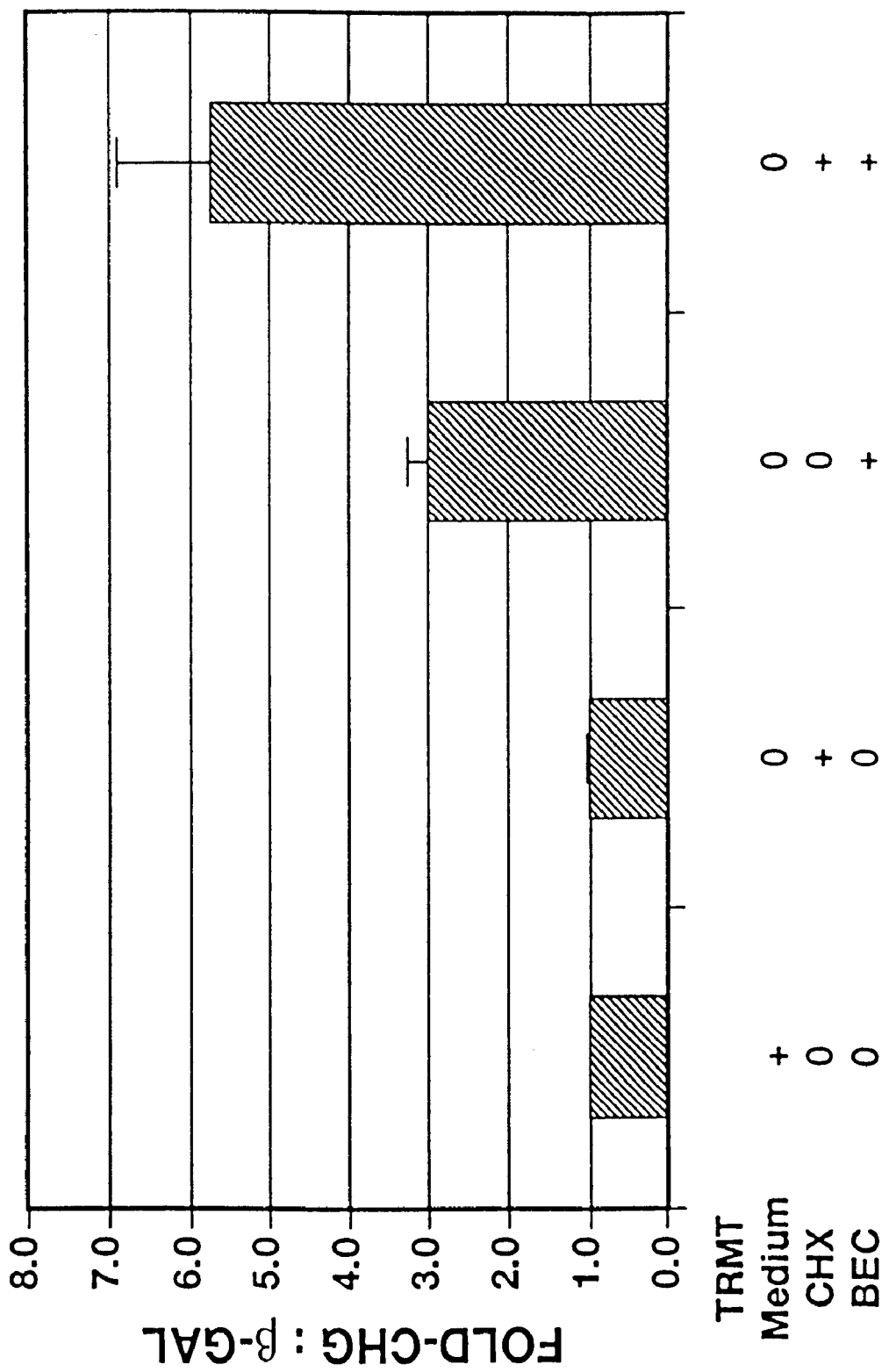
FIG. 8 shows that protein synthesis is not required for beclomethasone-mediated enhancement of β-gal activity. Cells were treated with either medium or CHX (10 μg/ml) for 30 minutes. Cells pretreated with medium were subsequently treated for 4 hours with either medium or beclomethasone at $10^{-6}$ M. Cells pretreated with CHX were subsequently treated with either CHX or $10^{-6}$ M beclomethasone+CHX for 4 hours. Cells were transfected with 1 μg/ml of pCMVβgal and 4 μg/ml DMRIE/DOPE. β-gal activity was determined using a CPRG microtiter assay. Results represent the average and SD from 2 experiments. Fold change BEC=β-gal activity in beclomethasone-treated cells/β-gal in medium-treated cells. Fold-change beclomethasone+CHX=β-gal activity in beclomethasone+ CHX treated cells/β-gal activity in CHX-treated cells.

As can be seen in FIG. 8, CHX moderately suppressed the β-gal activity in control cells, most likely by blocking synthesis of the β-gal protein (comparing the pCMVβ-gal plus and minus CHX). In contrast, beclomethasone-mediated enhancement of β-gal activity was still seen in cells treated with beclomethasone+CHX. In fact, the beclomethasone-mediated enhancement of β-gal activity was even greater in the presence of CHX. These results demonstrate that for beclomethasone to augment β-gal activity protein synthesis was not required.

EXAMPLE 16

BEC Effect on pCMVβ-gal mRNA Levels in A549 Cells

Figure 9:
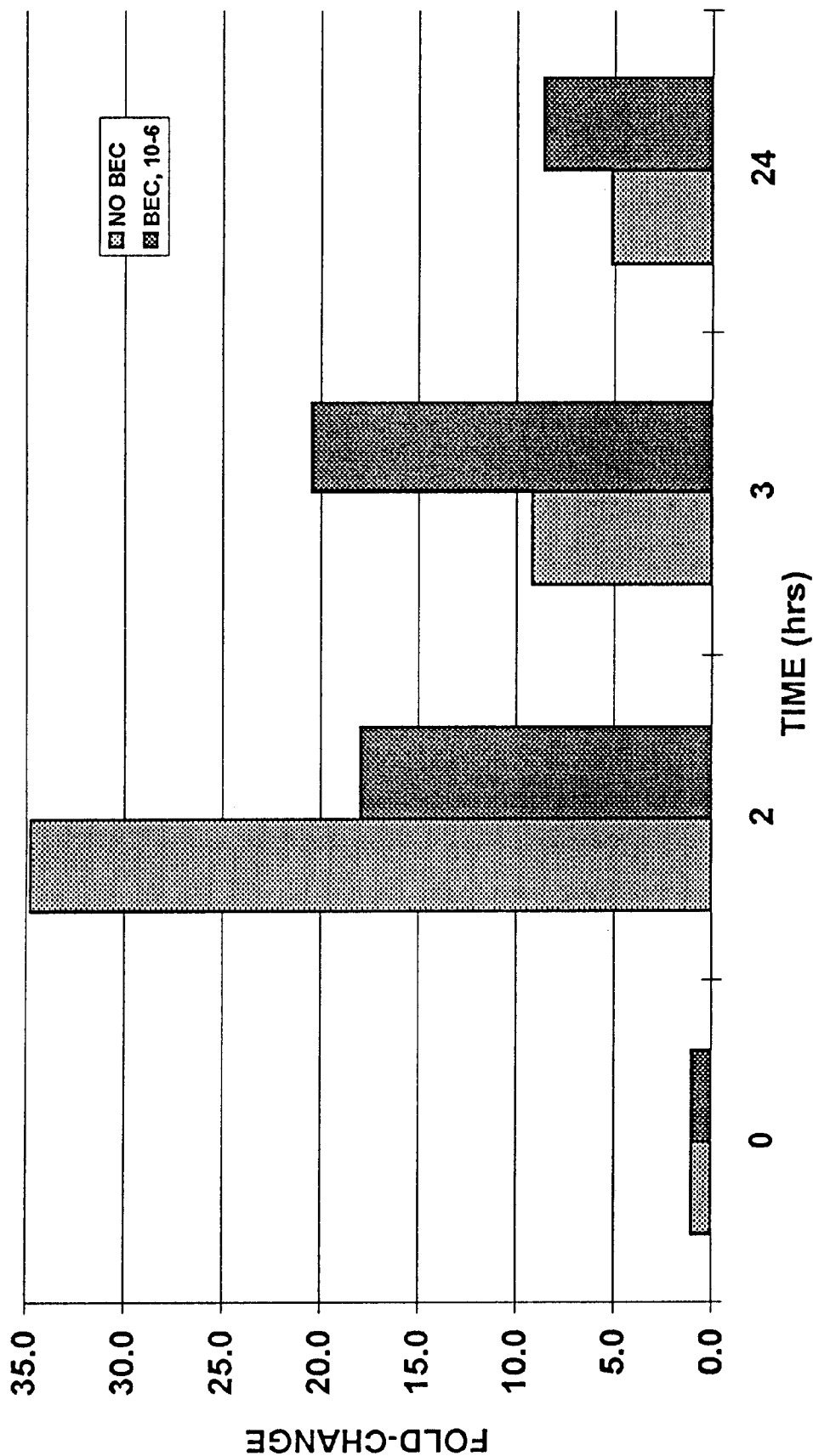
FIG. 9 shows that beclomethasone increased steady-state mRNA levels in A549 cells. A549 cells were treated with $10^{-6}$ M beclomethasone or medium for 4 hours. Cells were transfected with 1 μg/ml pCMVβgal plus 4 μg/ml DMRIE/ DOPE. At times specified (hours) after transfection, total RNA was harvested, converted to cDNA and specific βgal messages amplified by RS-PCR as described below. RS-PCR samples were resolved on a 1% TAE agarose gel and transferred to nylon filter. Filter was hybridized to a $^{32}$P-labeled βgal probe. Filter was analyzed by betascanner and bands of the appropriate size counted. Fold-change= βgal CPM in beclomethasone treated cells/βgal. CPM in medium-treated cells.

To establish kinetics of β-gal gene expression, A549 cells were transfected with pCMVβ-gal-DMRIE/DOPE. At various times after transfection was complete (2.5 hours), total RNA was harvested at T=2, 3, 7, 11, and 24 hours. mRNA was detectable by 2 hours and remained high for the entire period of time examined (data not shown). Once the kinetics of β-gal gene expression were established, A549 cells were pre-treated with medium or 10$^{-6}$ M beclomethasone for 4 hours, then transfected for 2.5 hours with pCMVβ-gal. Total RNA was harvested at T=0, 2, 3 or 24 hours and thereafter, mRNA levels determined by RS-PCR. While the mRNA levels were high in untreated as well as beclomethasone-treated cells by T=2 hours (38- and 18-fold induction, respectively), by T=3 and T=24 hours a definite increase in steady-state m RNA levels was detectable in the beclomethasone dipropionate-treated cells (FIG. 9). These results demonstrate that either transcription was increased or that the mRNA was stabilized in the cytoplasm by glucocorticoids.

The present invention demonstrates that glucocorticoids enhanced expression of reporter genes transfected into cells by cationic lipid-mediated transfection. The glucocorticoid effect was not dependent on a particular cationic lipid, vector promoter, vector reporter gene or cell type. Instead, the glucocorticoids effect was a general phenomenon related to glucocorticoids, as other steroids such as estrogen, progesterone or cholesterol did not enhance reporter gene expression with either of two promoters driving the β-gal gene. Glucocorticoids did not appear to function by increasing plasmid uptake by the cells, but in some fashion, enhanced expression of the reporter gene. A minimum of 3–4 hours of exposure with glucocorticoids was required to see the enhancement of gene expression. New protein synthesis was not required for beclomethasone-augmented reporter gene activity and CHX did not increase gene expression in the absence of beclomethasone dipropionate, suggesting that the superinduction seen in the presence of CHX may be glucocorticoids-specific.

The glucocorticoid effect was seen in A549, a human lung cancer cell line as well as primary rat lung cell isolates. The glucocorticoid-directed increase in βgal activity was not seen in COS-1monkey kidney cells transfected with pCMVβgal-DMRIE/DOPE. It is possible that COS-1 cells lack a receptor for glucocorticoids or lack some other glucocorticoid-sensitive intracellular factor involved in the enhanced response. A cell line which does not respond to the glucocorticoid effect may be useful in clarifying the exact nature of this response.

Most likely, a greater enhancement of β-gal activity by beclomethasone in the presence of lipopolysacchride (FIG. 4) would have been seen if the $10^{-7}$ M beclomethasone concentration was used instead of the $10^{-6}$ M concentration, which was less effective than was $10^{-7}$ M in the primary rat cultures. This modification is being examined, along with an intermediate concentration $5\times10^{-7}$ M.

lipopolysacchride was present in the plasmid preparations used and in virtually every other plasmid preparation made in most laboratories. Removal of lipopolysacchride from plasmid is a obstacle that will need to be overcome when using gene therapy clinically.

Whether the lipopolysacchride is in the plasmid or found pre-existing in inflamed lungs, the ability of the beclomethasone to reverse the inhibitory effects of lipopolysacchride or IL-1β, and possibly other cytokines or immune processes should be of great importance for gene therapy in the clinic.

The mechanism of the glucocorticoid-mediated enhancement of reporter gene expression has only just begun to be elucidated. Glucocorticoids have been shown to have numerous regulatory properties that are dependent on glucocorticoids concentration, cell type, and target gene or intracellular cite. Glucocorticoids may be imposing regulation on the immune response; genes known to be downregulated by glucocorticoids include IL-1β gene, TNF-α, intracellular adhesion molecule-1 (ICAM-1) as well as structural genes which make up the extracellular matrix such as collagen and stromelysin. Glucocorticoids have been shown to regulate gene by several different mechanisms such as decreasing gene transcription as seen for IL-1β gene but glucocorticoids also affect IL-1β expression at a post-transcriptional step.

Glucocorticoids also upregulate gene expression. The glucocorticoid receptor after interaction with glucocorticoids, directly binds to regulatory elements, i.e., a specific DNA sequence known as the glucocorticoid response element (GRE). In a glucocorticoid-responsive gene promoter the binding of the GC-glucocorticoid receptor complex upregulates transcription of the gene. Alternatively, the glucocorticoid receptor has been shown to bind to other transcription factors, such as c-fos or c-jun which, in the absence of glucocorticoid-receptor, activate gene transcription. By the glucocorticoid-receptor-c-fos or c-jun association, c-fos, c-jun are unavailable to activate responsive genes.

In the present invention, neither of the promoters used have the more common GREs, as determined by searching the gene bank of sequences. Messenger RNA half-life might have been extended due to the glucocorticoid-mediated inhibition of an mRNA-specific endonuclease but since CHX did not superinduce gene expression in the absence of beclomethasone, the inhibition of the endonuclease must also have some specificity for glucocorticoids. Alternatively, a cofactor which enhances transcription or translation, a co-factor for which new protein synthesis is unnecessary, may be positively modulated by glucocorticoids, thus enhancing production of the reporter gene protein.

A recent study by Liu et al. showed dexamethasone (DEX) augmented reporter gene activity, when it was coupled to a segment of the somatostatin promoter. The mechanism was shown not to involve the classic GRE in the promoter but instead, glucocorticoids receptor showed cooperative activity with a protein, cAMP regulatory element binding protein, (CREB) known to bind another transcriptional element, cAMP regulatory element (CRE). Both cAMP and protein kinase A were involved in Dex-mediated enhancement of reporter gene activity. A similar situation has been shown for the PEPCK gene; glucocorticoids upregulated and cAMP augmented transcription. In the present invention, the glucocorticoids effect shown here was not specific to, a single promoter region. That is, glucocorticoids enhanced β-gal activity from vectors that had either the SV40 promoter or the CMV promoter. It is unlikely that both of these promoters have similar CRE sequences in their promoters, but this possibility is not known.

Another study showed the positive effects of cell proliferation on transfected gene expression. Similar to what was seen herein, an increase in reporter gene uptake was not observed but, a 10-fold increase in luciferase activity was seen in cells stimulated to proliferate by cell injury. It is unlikely that glucocorticoids may have induced cell proliferation in the studies of the present application, since the cell density of the A549 or lung cells was such that the cells were in log growth phase for the entire incubation period of 48 hours.

Glucocorticoids have been used in the clinic for many years and are considered safe and effective. Patients with chronic lung inflammatory disease are good candidates for topical treatment with glucocorticoids delivered as an aerosol. In addition, glucocorticoids treatment has been shown to improve overall lung function in patients with cystic fibrosis, especially if the treatment is given early in the course of disease.

Considering the safety of glucocorticoids and the cost of gene therapy, which consists of expensive preparations of DNA and cationic lipid and, considering the potential side effects of the repeated delivery of large quantities of DNA-lipid makes the present invention all the more intriguing, both in terms of gene therapy as well as the molecular biology of glucocorticoids.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of increasing the cellular expression of a gene in lung tissue in an animal to treat a pathophysiological state of said animal, comprising the steps of:

administering to said animal an aerosolized cationic lipid:vector complex to said lung tissue, said lipid:vector complex adapted to express said gene in said lung tissue, wherein said gene is under control of a promoter that does not have a glucocorticoid response element and wherein expression of said gene treats the pathophysiological state of said animal; and administering to said animal a pharmacologically effective dose of an aerosolized glucocorticoid in an amount sufficient to increase the cellular expression of said gene, wherein the increase in the expression of said gene in said lung tissue enhances the treatment of the pathophysiological state of said animal.

2. The method of claim 1, wherein said glucocorticoid is budesonide or dexamethasone.

3. The method of claim 1, wherein said glucocorticoid is administered in a dose of from about 0.1 mg/kg to about 50 mg/kg.

4. The method of claim 1, wherein said glucocorticoid is in a form selected from the group consisting of a lipid soluble form, ethanol soluble form and a water soluble form.

5. The method of claim 1, wherein said glucocorticoid is administered concurrently with the administration of said lipid:vector complex, prior to administration of said lipid:vector complex or after administration of said lipid:vector complex.

6. The method of claim 1, wherein said animal is a human or a non-human animal.

7. The method of claim 1, wherein said glucocorticoid is a synthetic glucocorticoid or a non-synthetic glucocorticoid.

8. The method of claim 1, wherein said gene is selected from the group consisting of a recombinant gene, a native gene, a cDNA and an oligomer.

9. The method of claim 1, wherein said glucocorticoid enhances the expression and/or activity of a gene contained in a plasmid or viral vector.

10. The method of claim 1, wherein said glucocorticoid enhances the activity of a promoter.

11. A method of enhancing treatment of a pathophysiological state in a human by increasing cellular expression of a gene, comprising the steps of:

administering to said human an aerosolized cationic lipid:vector complex to said lung tissue, said lipid:vector complex adapted to express said gene in said lung tissue, wherein said gene is under control of a promoter that does not have a glucocorticoid response element and wherein administration of said gene treats the pathophysiological state of said human; and administering to said human a pharmacologically effective dose of an aerosolized glucocorticoid in an amount sufficient to increase the cellular expression of said gene, wherein the increase in the expression of said gene in said lung tissue enhances the treatment of the pathophysiological state of said human.

* * * * *

UNITED STATES PATENT AND TRADEMARK OFFICE
CERTIFICATE OF CORRECTION

PATENT NO.   : 6,656,916 B1
DATED        : December 2, 2003
INVENTOR(S)  : Lindsay Schwarz, Vernon Knight and Jennifer Lee Johnson It is certified that error appears in the above-identified patent and that said Letters Patent is hereby corrected as shown below:

Column 1,
Line 64, please delete the colon after "about".

Column 2,
Line 38 and 47, please delete the colon after "of".

Column 3,
Line 8, "βgalactosidase" should read -- β-galactosidase --.

Column 4,
Line 6, please delete the space after "$^{14}$C".
Line 10, "beclom-ethasone" should read -- beclo-methasone --.

Column 5,
Line 16, please replace the semicolon with a period.
Lines 19 and 27, please delete the colon after "of".

Column 6,
Line 31, please delete the colon after "cells".
Line 34, please delete the colon after "salt".
Line 50, "*Typhimurium*" should read -- *typhimurium* --.

Column 7,
Line 54, please delete the space after "β".

Column 8,
Line 46, please insert a space between "pH 9.0," and "50 mM".
Line 48, please insert a comma after "Madison".

UNITED STATES PATENT AND TRADEMARK OFFICE
CERTIFICATE OF CORRECTION

PATENT NO.     : 6,656,916 B1
DATED          : December 2, 2003
INVENTOR(S)    : Lindsay Schwarz, Vernon Knight and Jennifer Lee Johnson It is certified that error appears in the above-identified patent and that said Letters Patent is hereby corrected as shown below:

Column 9,
Line 3, please delete the colon after "IL".
Line 26, "FIG. 2*b*" should read -- FIG. 2B --.
Line 36, "Glucocorticoid-treatment" should read -- Glucocorticoid Treatment --.
Line 47, please delete the space after "β".
Line 47, please delete the comma after "cells".

Column 10,
Line 26, please delete the comma after "beclomethasone".
Line 30, "lipopolysacchride-suppressed" should read -- lipopolysacchride suppressed --.
Line 50, please insert a comma after "β-gal".
Line 59, "beclomethasone treated" should be hyphenated.

Column 11,
Line 19, please delete the comma after "and".
Line 64, "D-gal" should read -- β-gal --.

Column 12,
Line 8, please delete the comma after "plus".
Line 58, "m RNA" should read -- mRNA --.

Column 13,
Line 14, "glucocorticoids-specific" should read -- glucocorticoid-specific --.
Line 18, please insert a space between "COS-1" and "monkey".
Line 32, "lipopolysacchride" should read -- Lipopolysacchride --.
Line 41, please insert a comma after "processes".
Line 55, please insert a comma after "gene".
Line 60, please delete the comma after "glucocorticoids".

UNITED STATES PATENT AND TRADEMARK OFFICE
CERTIFICATE OF CORRECTION

PATENT NO.   : 6,656,916 B1
DATED        : December 2, 2003
INVENTOR(S)  : Lindsay Schwarz, Vernon Knight and Jennifer Lee Johnson It is certified that error appears in the above-identified patent and that said Letters Patent is hereby corrected as shown below:

Column 14,
Line 8, please insert a comma after "endonuclease".
Line 17, "(DEX) augmented" should read -- (Dex)-augmented --.
Line 24, "Dex-mediated" should read -- DEX-mediated --.
Lines 28 and 48, "glucocorticoids" should read -- glucocorticoid --.
Line 29, please delete the comma after "to".
Line 37, please delete the comma after "but".
Line 54, please insert a comma after "lipid".
Line 54, please delete the comma after "and".
Line 56, "makes" should read -- make --.

Signed and Sealed this

First Day of June, 2004

JON W. DUDAS
*Acting Director of the United States Patent and Trademark Office*